(12) United States Patent
Jeremy (10) Patent No.: US 10,885,337 B2
(45) Date of Patent: Jan. 5, 2021

(54) EXTERNAL VISUAL ENHANCEMENT AND CORRECTION SYSTEM

(71) Applicant: Cekan Jeremy, Champaign, IL (US)

(72) Inventor: Cekan Jeremy, Champaign, IL (US)

(73) Assignee: BLACK ASH TECHNOLOGIES, Houston, TX (US)

( * ) Notice: Subject to any disclaimer, the term of this patent is extended or adjusted under 35 U.S.C. 154(b) by 247 days.

(21) Appl. No.: 16/321,246

(22) PCT Filed: Nov. 9, 2018

(86) PCT No.: PCT/US2018/060005
§ 371 (c)(1),
(2) Date: Jan. 28, 2019

(87) PCT Pub. No.: WO2019/094705
PCT Pub. Date: May 16, 2019

(65) Prior Publication Data
US 2020/0210705 A1    Jul. 2, 2020

Related U.S. Application Data

(60) Provisional application No. 62/584,258, filed on Nov. 10, 2017.

(51) Int. Cl.
*G16H 10/60* (2018.01)
*G06K 9/00* (2006.01)
*H04N 5/225* (2006.01)

(52) U.S. Cl.
CPC ......... *G06K 9/00671* (2013.01); *G16H 10/60* (2018.01); *H04N 5/2253* (2013.01)

(58) Field of Classification Search
CPC .................. G06K 9/00671; H04N 5/2253
See application file for complete search history.

(56) References Cited

U.S. PATENT DOCUMENTS

| | | |
|---|---|---|
| 8,543,061 B2 | 9/2013 | Suhami |
| 8,725,842 B1 | 5/2014 | Al-Nasser |
| 9,148,717 B2 | 9/2015 | Shaffer |
| 9,310,891 B2 | 4/2016 | Rafii et al. |
| 2016/0299569 A1 | 10/2016 | Fisher et al. |

OTHER PUBLICATIONS

USPTO, International Preliminary Examination Report, in related application PCT/US18/60005, dated May 12, 2020, 7 pages.
USPTO, International Search Report, in related application PCT/US18/60005, dated Nov. 9, 2018, 3 pages.
USPTO, Written Opinion of the International Search Authority, in related application PCT/US18160005, dated Nov. 8, 2018, 4 pages.

*Primary Examiner* — Jitesh Patel
(74) *Attorney, Agent, or Firm* — D'Hue Law LLC; Cedric A. D'Hue (57) ABSTRACT

A external visual enhancement and correction system is shown comprising a head-worn device and a watch face, the head-worn device including a frame defining a lens aperture, a temple mounted to the frame by a hinge, a pair of cameras mounted into the frame, at least one battery with connectors and at least one Bluetooth 4.0 transceiver encased in the hinge of the temple, an OLED display mounted in the lens aperture of the frame, and a plurality of charging ports mounted into the frame, the watch face including a top frame having a home button, a touchpad, a computer, a memory, a Bluetooth 4.0 transceiver, and a bottom frame.

1 Claim, 9 Drawing Sheets

Figure 15 ations, and other industries. There have been various technologies all building and changing the market of mainstream technology, but not always addressing the consumer with special needs who relies on technology. There is a need for a better way of granting and gaining independence for consumers who rely on assistive technology.
EXTERNAL VISUAL ENHANCEMENT AND CORRECTION SYSTEM

CROSS REFERENCE

This application is the national stage application of PCT international patent application serial number PCT/US18/60005, filed Nov. 9, 2018 which claims priority to U.S. provisional patent application 62/584,258, filed Nov. 10, 2017, the subject matter of each is expressly incorporated by reference.

FIELD

This disclosure is directed to an external visual enhancement and correction system.

BACKGROUND

History of the Invention

Smart Technology defines a new era in homes, telecommunications, and other industries. There have been various technologies all building and changing the market of mainstream technology, but not always addressing the consumer with special needs who relies on technology. There is a need for a better way of granting and gaining independence for consumers who rely on assistive technology.

Below is information about various current assistive technology devices, in particular head sets available for sale on the open market. The E-Sight (eSight Corporation, https://www.esighteyewear.com/) is the only device currently certified by the FDA and is currently covered by a plurality of U.S. Patents and published patent applications (U.S. Pat. Nos. 8,135,227, 8,494,298, 8,976,086, 9,372,348, 9,516,283, and 9,618,748; U.S. published patent application numbers 2013/0215147, 2013/0329190, 2015/0355481, 2016/0314564, 2017/0200296, and 2017/0235161). eSight is also front heavy due to the components placed on the face and secured magnetically with a strap around the head on special prescription glasses frames. The eSight headset has a problem of overheating during extended periods of use and is not intended to be used as such. Battery life is 2-4 hours at best. eSight comes with a limited 4 GB memory card. The device will not currently support anything larger. It is picture play back and magnification not real-time processing. The eSight device's autofocus feature does not work 12 inches or less.

NuEyes low vision glasses (NuEyes; https://nueyes.com/) offers wireless operation, 12× magnification with a telephoto lens (Needs additional components to increase magnification beyond 12×; Can only go to 8× without a telephoto lens), contrast control, and voice activation. Unfortunately NuEyes is not designed for long periods of use offering only 1-2 hours of battery life. The NuEyes device can overheat when used and its electronics are not fully incorporated in the frames. The device comes in pieces and not all buttons are on the wireless remote. The power button and modifier buttons are only on the left temple. A user of NuEyes is not licensed to drive. The user must walk with caution and other warnings.

These devices include several flaws. They are not a single piece of equipment: each the E-Sight and the NuEyes are separate electronics and separate pieces. They do not address individual needs of each client in each instance. They are not designed for continuous operations. Neither are capable of shipping overseas and are not designed for public places.

SUMMARY

The Ash 1 meets needs of the Smart Technology era.

A external visual enhancement and correction system comprising a head-worn device and a watch face, the head-worn device including a frame defining a lens aperture, a temple mounted to the frame by a hinge, a pair of cameras mounted into the frame, at least one battery with connectors and at least one Bluetooth 4.0 transceiver encased in the hinge of the temple, an OLED display mounted in the lens aperture of the frame, and a plurality of charging ports mounted into the frame, the watch face including a top frame having a home button, a touchpad, a computer, a memory, a Bluetooth 4.0 transceiver, and a bottom frame.

The Ash 1 software system starts with the Digital Prescription Software known simply as Video Analytical Stream Interface For Correction and Enhancement or (VASICE). VASICE creates a digital prescription, a new concept developed for the Ash 1 Glasses and the new era. It is made up of Digital Gates or Adjustable Filters, each gate will govern a certain attribute for the entire interface. The Governing Perimeters are set during a regular doctor visit for the wearer along with an Ash 1 technician. Modification of VASICE can be based on individual needs or work environments. Names of gates or operating system are subject to change pending project development and testing.

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein.

Corresponding reference characters indicate corresponding parts throughout the several views. Although the drawings represent embodiments of the present disclosure, the drawings are not necessarily to scale and certain features may be exaggerated in order to better illustrate and explain the present disclosure.

DETAILED DESCRIPTION OF THE EXEMPLARY EMBODIMENTS

The embodiments disclosed below are not intended to be exhaustive or limit the disclosure to the precise forms disclosed in the following detailed description. Rather, the embodiments are chosen and described so that others skilled in the art may utilize their teachings.

The term "frame" refers to the portions of the glasses surrounding the lens. The left frame surrounds the lens for the left eye of the wearer while the right frame surrounds the lens for the right eye of the wearer.

The term "bridge" refers to the portion of the glasses between the left and right frames.

The term "temple" refers to the portion of the glasses from the frame to the ear of the wearer. The temple tip, also known as the earpiece, is the portion of the temple typically behind the ear of the wearer.

The term "hinge" refers to the junction between the frame and the temple.

This disclosure covers the Ash 1 system. The Ash 1 is the next generation of assistive technology. Its benefits are not just for its inventor but for the community and members of society. Each section highlights the process it goes through from the start to finish, as well as the current technology breakthroughs that serve the particular function that makes the system.

Figure 1A:
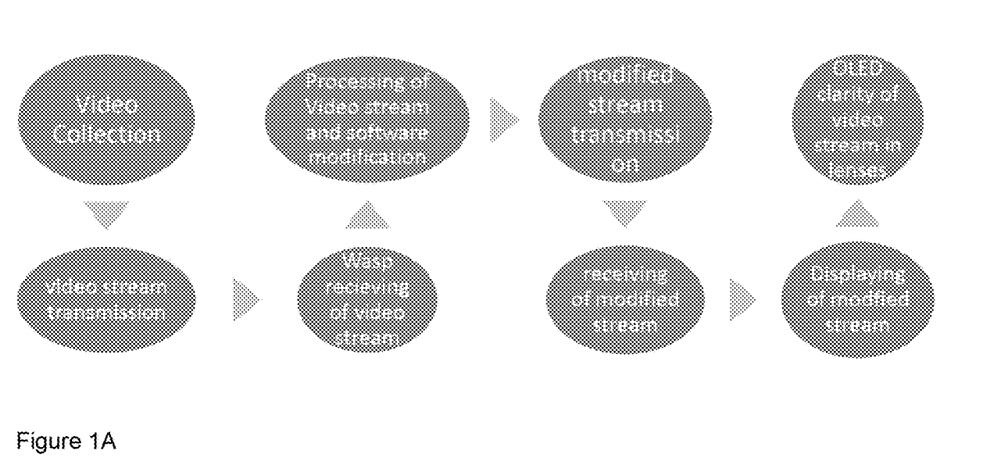
FIG. 1A is a schematic diagram of how an embodiment of the Ash 1 SBS system works.
Figure 1B:
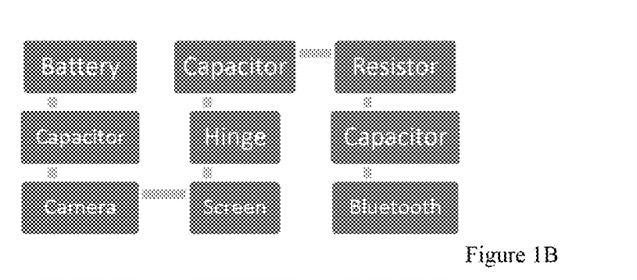
FIG. 1B is a schematic diagram of the electrical plan of the glasses of the ASH 1 SBS system.
Figure 1C:
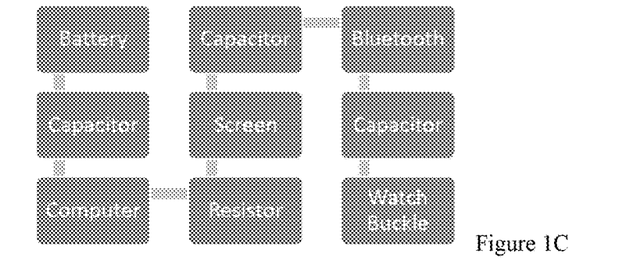
FIG. 1C is a schematic diagram of the electrical plan of the watch of the ASH 1 SBS system.

The glasses (101) are a real-time video transmission platform as illustrated by the process of the program in FIG. 1A. FIGS. 1B and 1C, respectively, illustrate the electrical plans of the glasses (101) and watch (301).

Figure 2A:
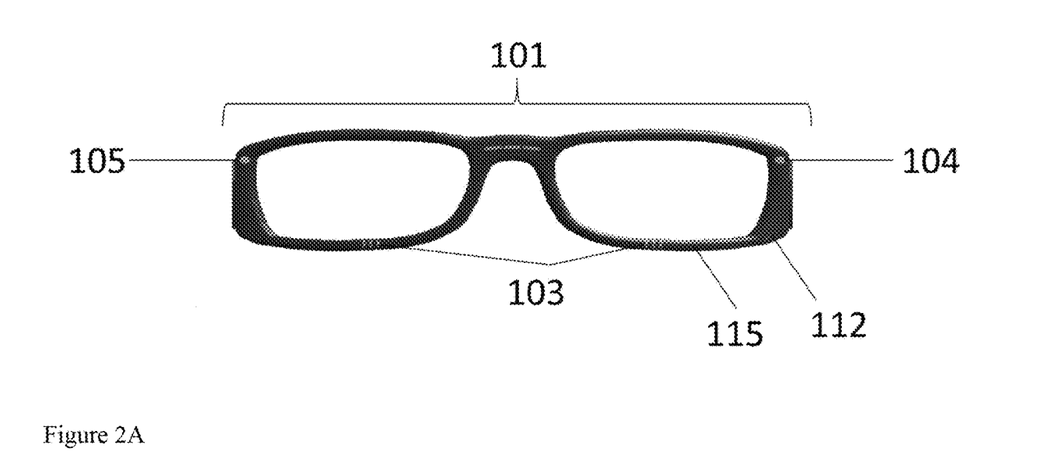
FIG. 2A is a front view of the glasses according to an embodiment of the ASH 1 SBS system.
Figure 3:
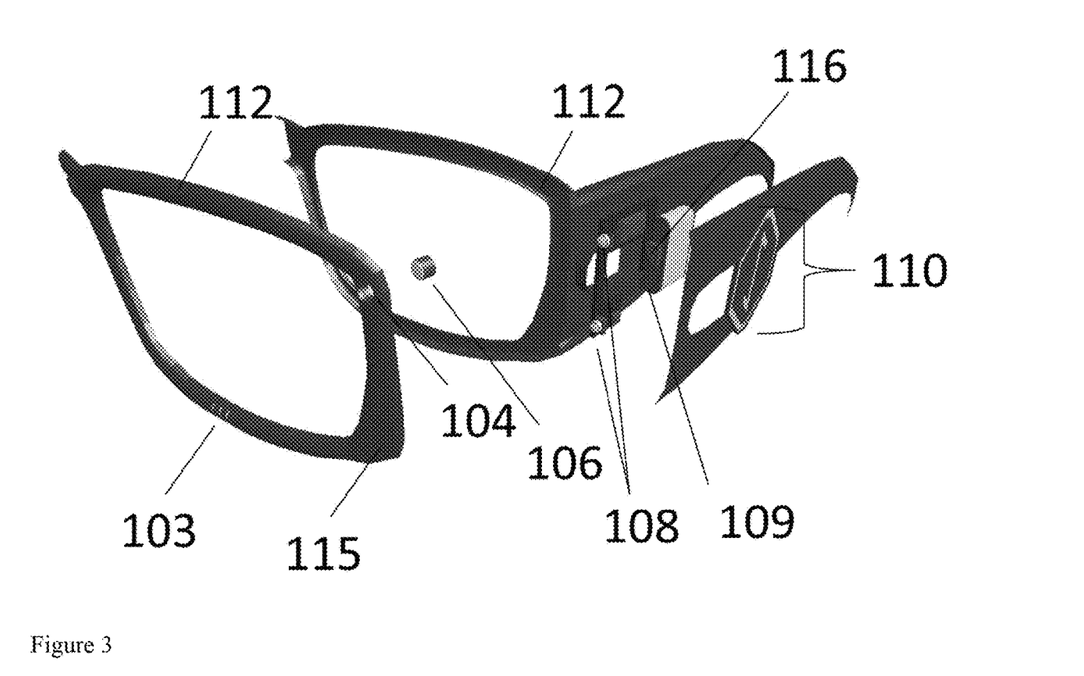
FIG. 3 is an exploded view of the glasses according to an embodiment of the ASH 1 SBS system.

FIGS. 2A and 3 show the front of the glasses (101) with cameras (106) mounted in the top left of the left frame (104) and top right of the right frame (105). The mountings will be a micro USB connection since the cameras use micro USB males and provide 85 frames per second (fps). The addition of cameras (106) on the frame (110) edges 104 and 105 allows for a panoramic view instead of the limited view in other devices and allows the glasses (101) near duplication of field of view of the eye 202 (FIG. 11) (close to 180 degrees' side to side and 20 degrees of straight and down center). These positions will allow for optimization of cameras (106) to create a field of vision acceptable to the wearers (201) (FIG. 11) needs and avoid any disorientation. Integrating the cameras (106) into the glasses (101) instead of attaching will allow for future updates as better cameras (106) are researched and developed from suppliers or from in house research and development teams. It is envisioned that the components of Ash 1 SBS (100) can be integrated into mainstream glasses. With the popularity of drones rising in the USA and worldwide it is possible that the technology used in drones could help upgrade the video components of the glasses (101).

Pictured in FIG. 3 are charging ports (103) at the bottom 115 of the frames 112 allowing for case charging 401 (FIGS. 12A-14) or wireless pad charging.

The next phase in the process is transmission and the design of the left and right temples are important.

Figure 2B:
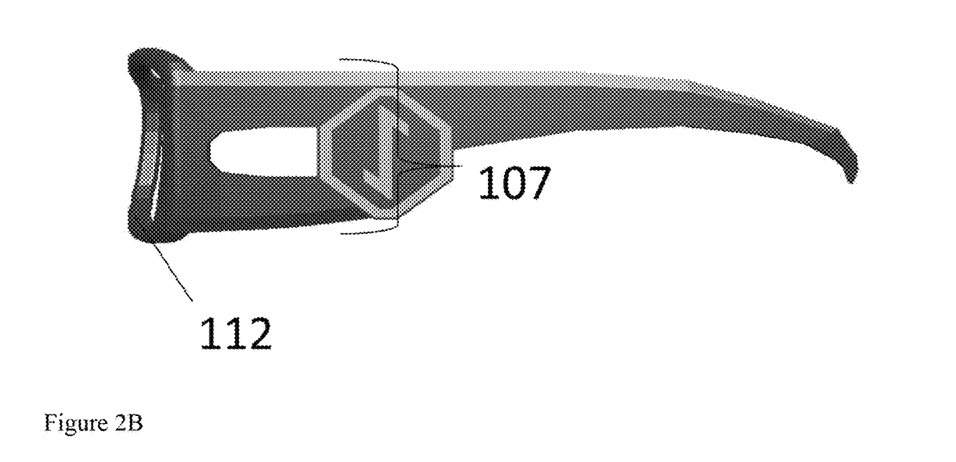
FIG. 2B is a side view of the glasses according to an embodiment of the ASH 1 SBS system.

As best illustrated by FIG. 2B, the thick design of the temple (107) serves two purposes. The first purpose is that the thick design serves as a shield for external light off the lenses. This allows for full use of the displays within the frames.

The second purpose best illustrated in FIG. 3, temple (107) houses the lightweight coin style battery packs (109) at 1000 mA and the Bluetooth 4.0 transceivers (116). The transceivers (109) works on a similar premise and function as of a First Person View system (FPVS) for drones. However, the most likely direction is the transceivers (109) will work on a custom and system specific Bluetooth or Wi-Fi capable applications. This gives two advantages it will work like a normal cell phone or work within any Wi-Fi establishment. FIG. 3 shows the exploded view of the temple (107) to show the components for connection as well as the hinge (108) including the camera (106) in the upper right part of the frame (104).

Figure 4:
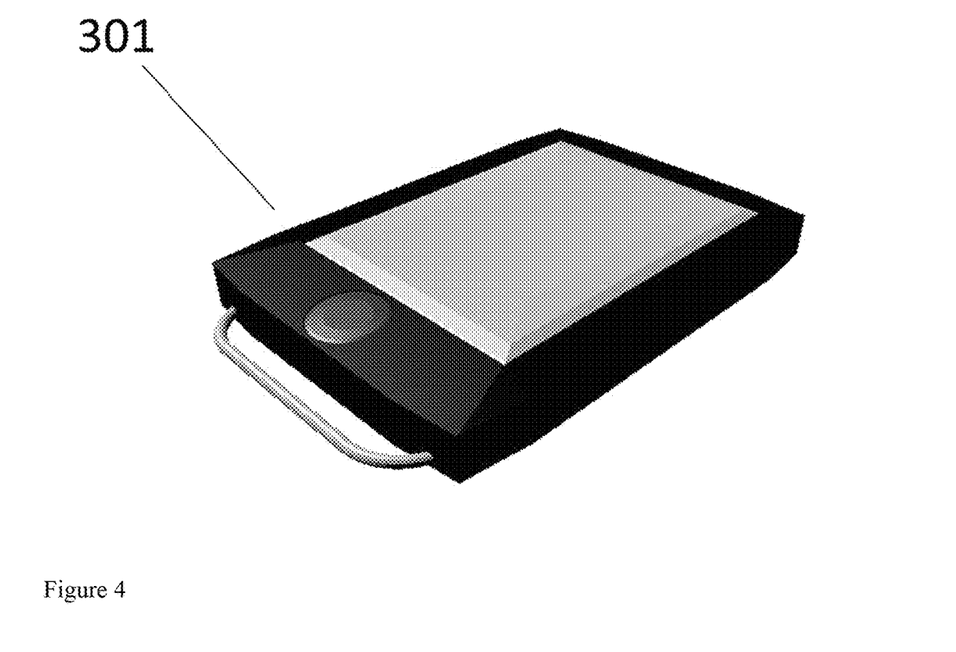
FIG. 4 is a perspective view of the watch face of the watch according to an embodiment of the ASH 1 SBS system.
Figure 5:
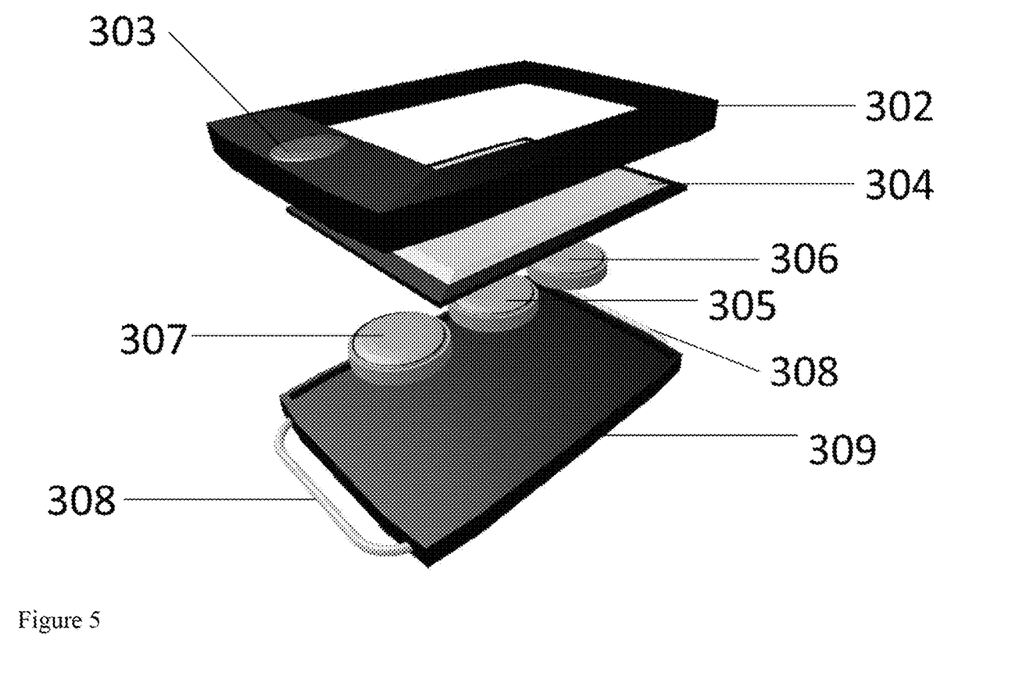
FIG. 5 is an exploded view of the watch face of the watch according to an embodiment of the ASH 1 SBS system.
Figure 6:
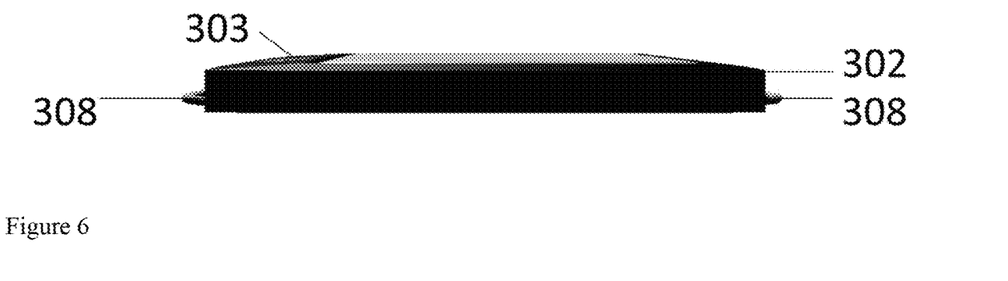
FIG. 6 is a side view of the watch face of the watch according to an embodiment of the ASH 1 SBS system.

The Ash 1 SBS work on a different principle than the pad of buttons principle. The glasses (101) work on the emerging premise of wearables and even Augmented Reality (AR) or Virtual Reality (VR), FIGS. 4, 5, and 6 are representations of the watch face (301) of the two part Ash 1 SBS system. FIG. 4 shows the watch face (301), a smart watch (301) built with a small computer (305) with a small transceiver (307). The watch face (301) also houses a small charging connection (not shown) housed in the end of the flexible wristband (not shown) to allow wireless mat charging and other forms of charging. FIG. 5 shows the exploded view of the watch face (301) including top frame (302) having home button (303), touchpad (304), computer (305), memory (306), transceiver (307), and bottom frame (309).

The watch face (301), also known as Wrist Applied System Processor or (WASP), provides the third function of this system, which is the processing power. Built to house 13 GB computer (305), an additional 16 GB memory card (306), and the transceiver (307) in watch face (301), watch face (301) is configured to be upgraded as time and design progresses. Software on this watch face (301) is configured to facilitate the cameras (106) as the collecting entity.

The Ash 1 software system incorporates the following gates: Collection, Compression, Background, Contrast, Brightness, Magnification, Entity Identification, and Splitter.

Collection Gate

First the collection Gate it is the gate that analyzes the digital video stream collecting the surroundings and identifying entities, within the video stream. The collection gate labels the overall picture color coding entities to respective gates for streamlined processing of the other gates coming directly from the camera sources.

Compression Gate

The compression gate has the purpose to compress video information from two camera sources (106) and feeds into one video feed which includes removing duplicates of all entities detected from the collection gate before moving on. The compression gate streamlines the processing load on the other gates.

Background Gate

The background gate helps with streamlining the process through the magnification and contrast gates. It does not process any other entities other than the entities that make up the background beyond other entities. It leaves those entities to other gates. These entities that are not identified as part of the background are ignored thus defining the background features in the image for better clarity of depth and to help reconstruct the image.

Autofocus: cleans up any video from the 85 images per second camera, which for it could take less than a second to assure video clarity.

Object identification: identify objects in an environment. This allows the wearer to autofocus on a vehicle or on a sign so that it could be easier to identify for the wearer.

Person identification: identify people in the environment, this could allow the wearer to see facial features or facial expressions. It is important to understand that reading body language is important so this could help the wearer be able to see a person and allow them to see accurate posture.

Text identification: self-explanatory for that this would help the wearer see texts in front of them such as newspapers, books, vehicle gauges or road signs. This is a feature that could even help with future applications.

Video stabilization: The program counteracts the bouncing of movement. This is to make sure that the images are clean and crisp so that the autofocus may do it required job. As well as telling the Displays pixel which to turn on or turn off for a clean and crisp image.

Color contrasting: With some conditions color dependent color contrasting will assure that depending on condition that the wearer is able to identify the appropriate color palate, it is not meant to make colors visible but more distinguished for the wearer.

Contrast Gate

The contrast gate governs the stream through the modification of light, shadow, gradients, and, color. The contrast gate makes the colors and outlines of entities sharper allowing for distinction and isolation of and between entities. The contrast gate builds off the background gate allowing entities for identifying by the wearer during doctor appointment. The contrast gate also treats different visual contrast problems.

Brightness Gate

The brightness gate builds off of the contrast gate entities. The brightness gate modifies the brightness of the feed. If the feed is something too bright then the brightness gate will tone down the brightness of that entity. If the entity is too dark then the brightness gate will be brightened up. This feature could help make the image that much sharper compounded with the contrast gate for the wearer when dealing in bright light or low light situations.

Magnification Gate

The magnification gate is used with the contrast and brightness gates. This magnification gate will add a magnification multiplier to all entities. The magnification gate further defines a entity for clarity to the wearer using the doctor's input during the appointment. The magnification gate also builds the image provided to the Entity Identification Gate to take the image and modify it allowing for easy identification of objects and sets the ability to identify other individuals. It could be used for far sighted individuals as well.

Entity Identification Gate

The entity identification gate is used to reconstruct the layers of the final image utilizing background, contrast, and magnification gates, allowing for deeper analyzation of the sharper images to identify moving entities such as people. The entity identification gate is used to identify organic entities from nonorganic entities. When an image or a portion of an image is identified as an organic entity the entity identification gate will analyze body and facial features. This is helpful so that the wearer can identify people from objects and identify features of another individual from other people.

Splitter Gate

The splitter gate further reconstructs the modified feed of the previous gates and will break down the feed to identify which part of the feed goes to which display. It is known that a person has two eyes therefore the device must have two displays set up so that a full view can be accommodated. The splitter gate can also be disabled for a person who is also mono-sighted or blinded in either eye.

Once the cameras (106) send the image through the transceiver (109) to the WASP (301) and into the software to be modified. Then the modified stream is wirelessly transmitted by transceiver (307) back to the glasses 101 to be put on to the screens 111 for display which is projected through a panoramic view much like normal vision. FIG. 6 shows the design of the watch head 301 to give that the perspective of a traditional smart watch.

Figure 7:
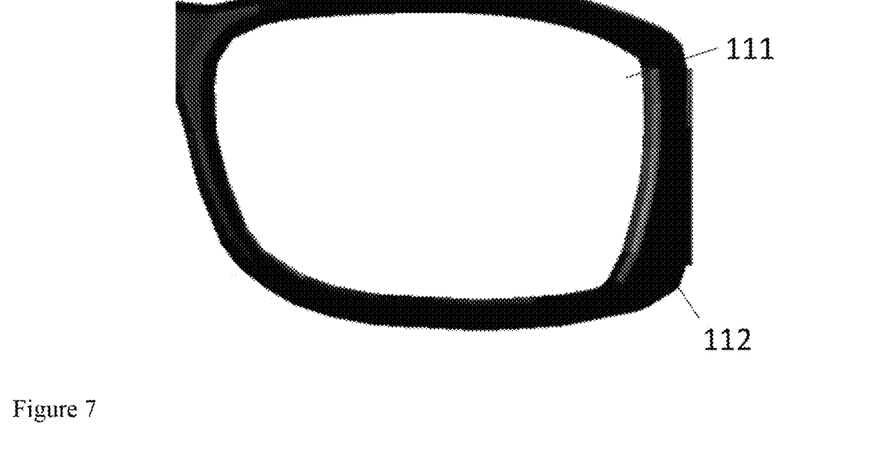
FIG. 7 is a front view of the frame and display of the glasses according to an embodiment of the ASH 1 SBS system.
Figure 8:
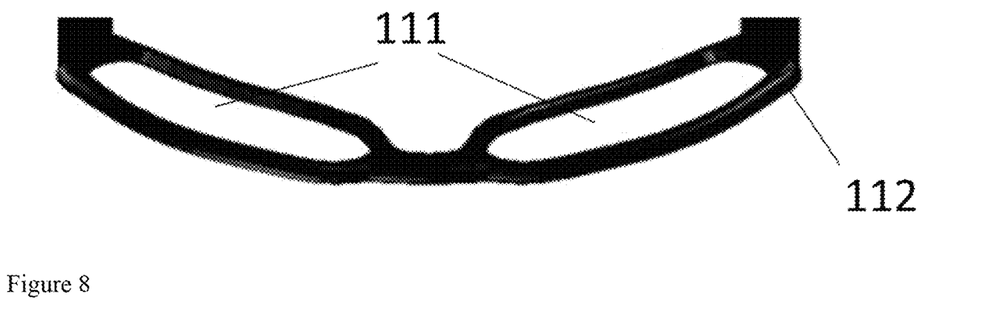
FIG. 8 is a top view of the frame and display of the glasses according to an embodiment of the ASH 1 SBS system.

FIGS. 7 and 8 illustrate the design of the overall look of the frame (112) and the display (111). Instead of lens, frame (112) houses the Organic Light Emitting Diode (OLED) screens (111) capable of AR & VR. FIG. 7 shows the reason for the advantages of the OLED flexibility with the emergence of flexible and curved televisions by the OLED. The displays (111) of the ASH 1 will be able to fit into the glasses frames (112). The following is the process of an OLED display (111) in the frames (112). Later as the technology further evolves the process of OLED display will include waveguide AR technology and projection under waveguide technology.

Batteries 109 of temple (107) will supply the power to the displays (111) through connectors between the frames (110) and temple (107).

First the electrical power is supplied through the entire frame (112) with a rubber seal to keep shorting and protection.

The function of the OLED (111) allows for the pixels to be turned on and off via the WASP (301) meaning only the software and OLEDs (111) present the images to the wearer (201) in their specific settings.

Figure 9:
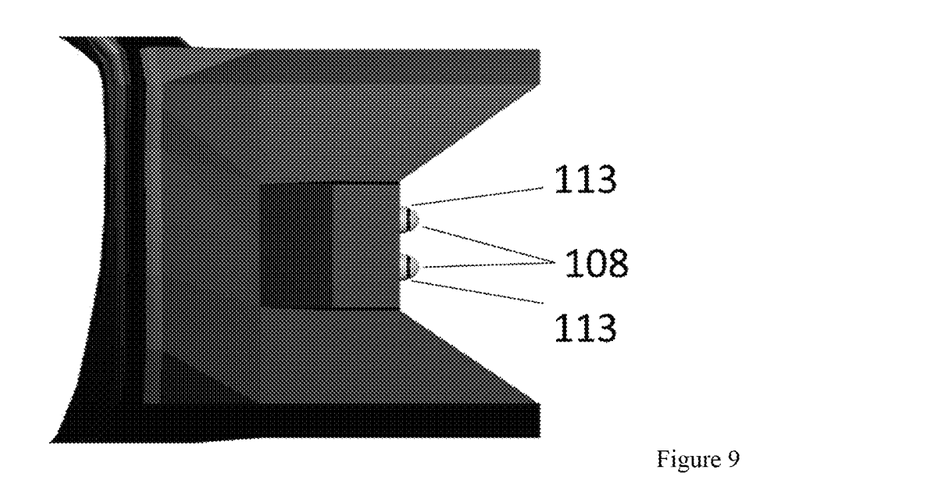
FIG. 9 is a side view of the temple of the glasses according to another embodiment of the ASH 1 SBS system.
Figure 10:
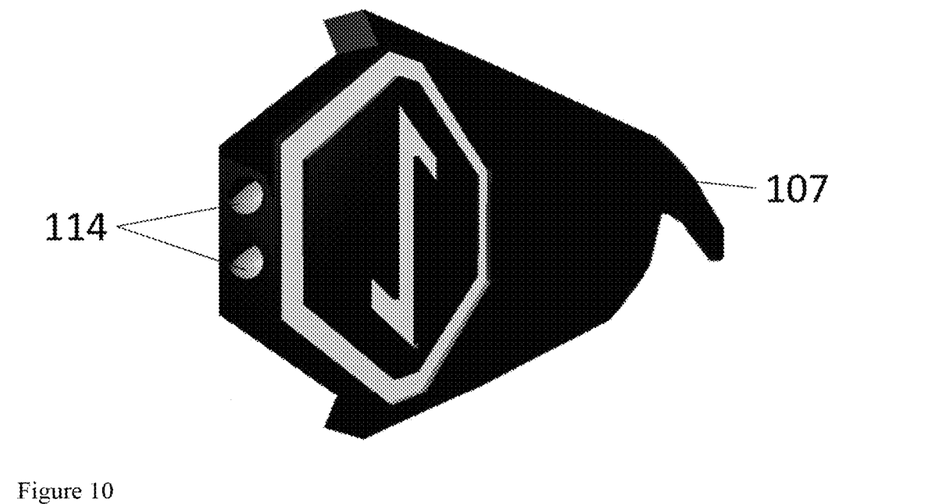
FIG. 10 is a side view of the frame of the glasses according to another embodiment of the ASH 1 SBS system.
Figure 11:
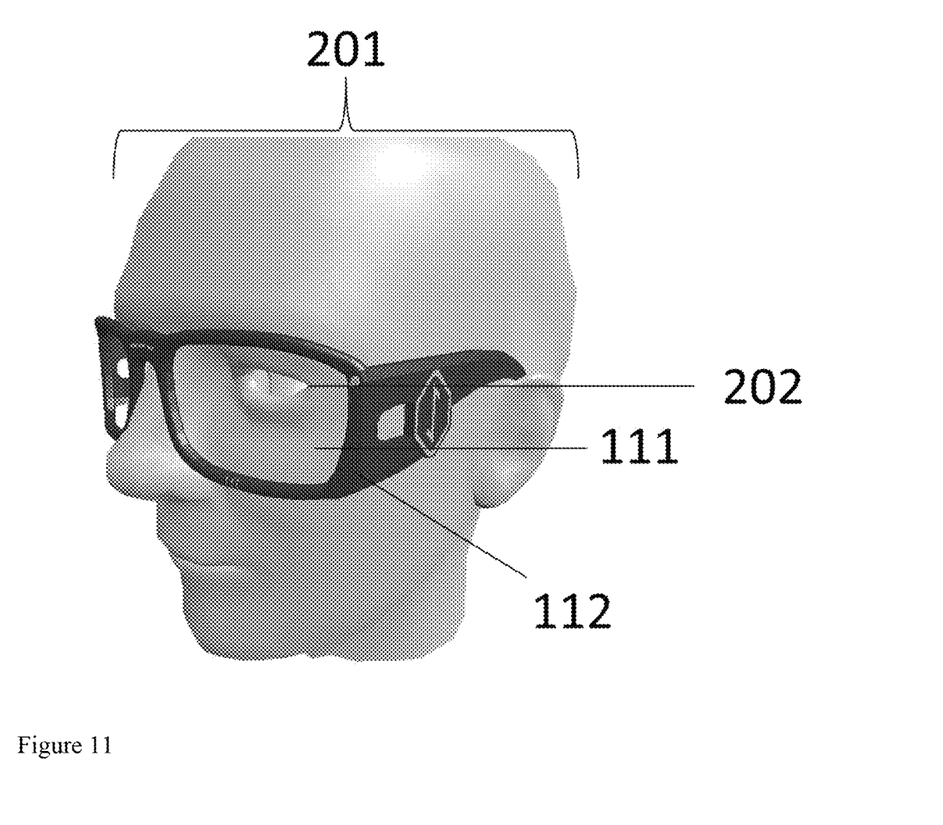
FIG. 11 is a perspective view of the glasses on a virtual wearer according to an embodiment of the ASH 1 SBS system.

Power for the ASH 1 SBS (100) is supplied through 4-6 coin configured batteries (109). Possible upgrades may include advances in battery technology and styles of electrodes. The coin battery (109) is designed to be easily integrated into the temples (107). FIG. 9 shows the area of the hinge (108) where the batteries (109) will be placed inside the logo (110). FIGS. 9 and 10 show the connections (113) and (114) between temple (107) and frame (112) that allows power distribution as well as connection 113 between the display 111 and video Transceiver 109. FIGS. 9-10 illustrate a different embodiment of the glasses than FIGS. 2A-3 and 11. Power for the ASH 1 SBS (100) is based on the same power distribution in modern headphones. The rubber rings (113) around the male connectors (108) (FIG. 9) keeps the power from shorting out, damaging the components and serving as a safety precaution. FIG. 11 shows a view of the entire glasses frames (112) are designed with the flexibility of standard glasses to allow for easy storage and folding into a standard sized case.

Figures 12A, 12B, 13:
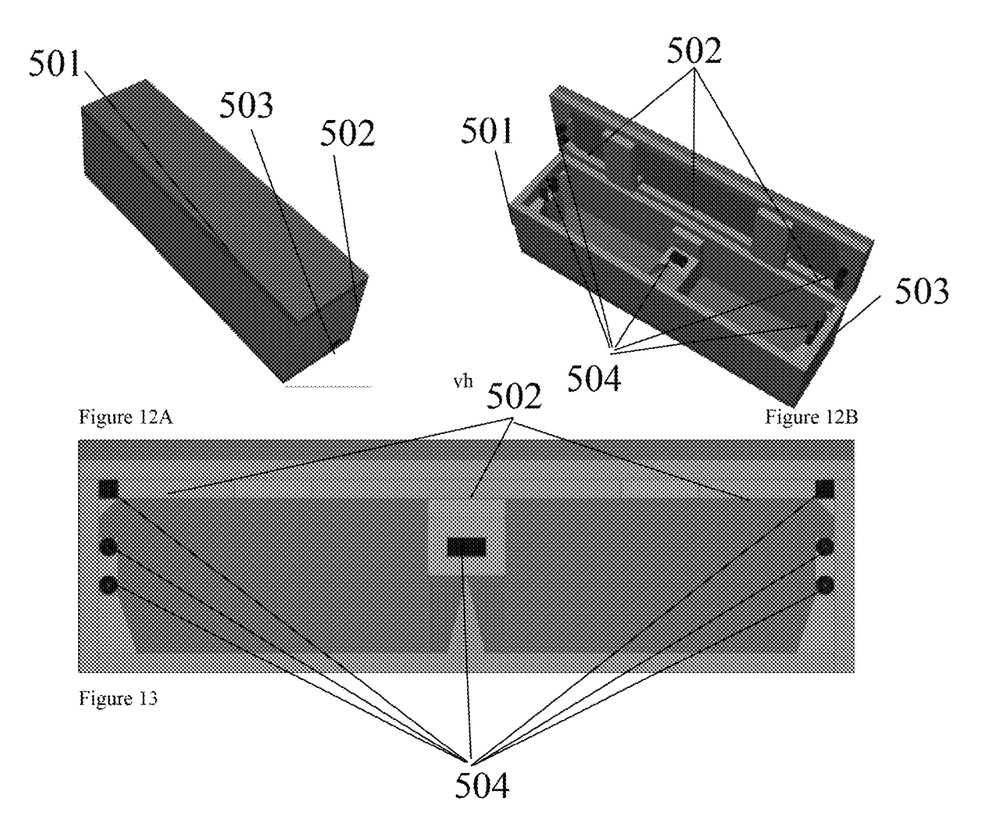
FIG. 12A is a perspective view of a closed glasses case according to an embodiment of the ASH 1 SBS system.
FIG. 12B is a perspective view of an open glasses case according to an embodiment of the ASH 1 SBS system.
FIG. 13 is a top view of an open glasses case according to an embodiment of the ASH 1 SBS system.
Figure 14:
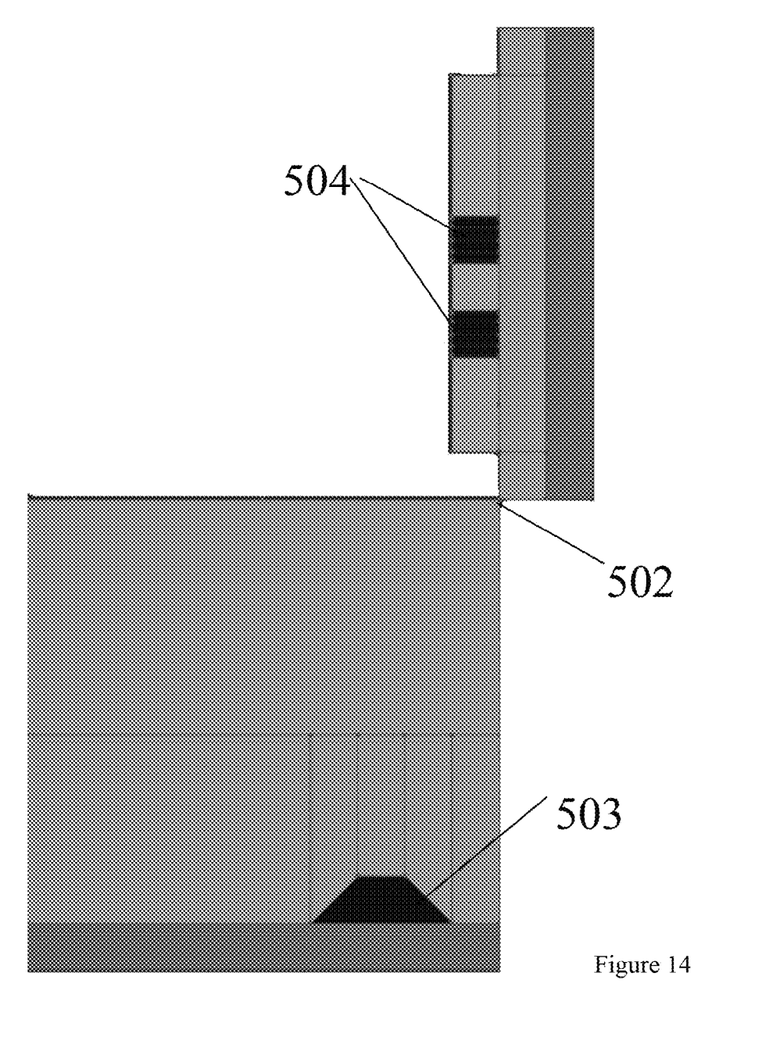
FIG. 14 is a side view of an open glasses case according to an embodiment of the ASH 1 SBS system.
Figure 15:
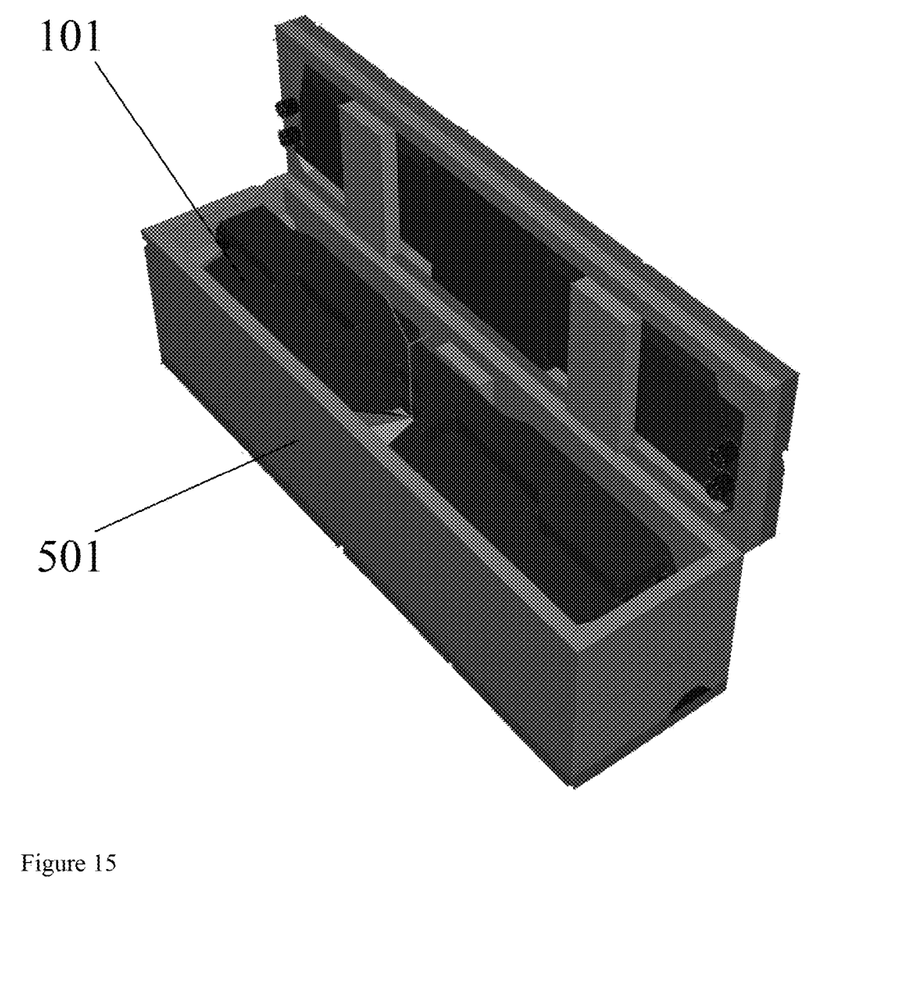
FIG. 15 is a perspective view of an open case with glasses according to an embodiment of the ASH 1 SBS system.

Maintenance will be quick and easy. The charging ports depicted in FIG. 2A-3 allow for the charging of batteries while sitting in the wireless charging standard case or able to be plugged in by the special connectors 108 in FIGS. 9 & 10 creating a complete circuit while sitting on the night stand. Though not depicted a screen safe cloth is envisioned for wiping and maintaining the OLED displays (111). It is recommended for best performance that charging be done during the night. FIGS. 12A-14 show the standard clam case 501 with hinges 502 for safekeeping and protection. FIG. 13 shows the wired features in the case with compressible connections 108 for when wired charging 504. However, the case comes in a wireless connection format without the compressible connections with both coming with a micro USB port 503 for connection to outlet depicted in FIG. 14. As best illustrated in FIG. 15, case 501 is shown holding glasses 101.

With maintaining as simple as possible and within the universal standard of having regular glasses the construction of the ASH 1 SBS including glasses (101) and its companion smart watch (301) also sets another standard in that the construction is meant for quick and easy production through 3D printing and forced mold injection. In addition to using recycled materials such as carbon composites and other materials from the surrounding community, the ASH 1 SBS uses an onyx carbon fiber composite frame with a force injected High Strength High Temperature Fiberglass. It is envisioned the ASH 1 will become a green system from production to maintenance later using solar cells to help with charging. This allows for easy replacement and speedy production to the point that a part is broken during use then Black Ash Technologies will provide the services to quickly repair the product because of the composite construction and the 3D printed method in short time. This will allow the products cost to be less than the current systems out there.

Personalization is the relationship between client and the product they use every day. With the software, we work with the client's doctor or vision specialist to make sure that each individual person's needs are met. There is no one person the same just like their vision is not the same. This product ability to be programed to the wearers' needs sets it apart from other systems in that if the vision is not the same then the products should not be the same for everyone. The same not only goes for the needs of the person but their likes/dislikes and personality. It is important that the 3D printing process allows the design of the product to be modified and varied depending on the style of the person who will wear the system. The color schemes and styles are still being designed and flushed out but it will be the game changing difference all assistive technologies seem to ignore. It will also serve the need of a community that current wearables seem to ignore outright.

It is clear by the explanation above that the Ash 1 has the potential to apply to other industries away from solely being a program for visual impairment. It can be applied in such fields as Law Enforcement such as suspect identification, Military readiness such as light weight alternatives to bulky and heavy night vision and low light vision systems. This is a 21st century that could find its way into a number of products and systems for the coming smart age.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A external visual, enhancement and correction system comprising:
   a head-worn device and a watch face, the head-warn device including
      a frame defining a lens aperture, a temple mounted to the frame by a hinge,
      a pair of cameras mounted into the frame,
      at least one battery with connectors and at least one Bluetooth 4.0 transceiver
      encased in the hinge of the temple,
      an OLED display mounted in the lens aperture of the frame, and
      a plurality of charging ports mounted into the frame,
   the watch face including
      a top frame having a home butt
      a touchpad,
      a computer,
      a memory, a Bluetooth 4.0 transceiver, and
      a bottom frame,
      wherein the computer utilizes software for visual enhancement or correction,
      wherein the software includes the following gates: collection, compression,
      background, contrast, brightness, magnification, entity identification, and splitter.

* * * * *